(12) United States Patent
Wakikaido et al.

(10) Patent No.: US 7,195,626 B2
(45) Date of Patent: Mar. 27, 2007

(54) ELECTRODE DEVICE FOR MICROWAVE SURGERY

(75) Inventors: Koichi Wakikaido, Osaka (JP); Yoshimasa Kurumi, Shiga (JP); Shigeyuki Naka, Shiga (JP); Shigehiro Morikawa, Shiga (JP)

(73) Assignee: Alfresa Pharma, Osaka (JP)

( * ) Notice: Subject to any disclaimer, the term of this patent is extended or adjusted under 35 U.S.C. 154(b) by 291 days.

(21) Appl. No.: 10/516,611

(22) PCT Filed: Jun. 2, 2003

(86) PCT No.: PCT/JP03/06958

§ 371 (c)(1),
(2), (4) Date: Dec. 3, 2004

(87) PCT Pub. No.: WO03/101324

PCT Pub. Date: Dec. 11, 2003

(65) Prior Publication Data

US 2005/0149009 A1 Jul. 7, 2005

(30) Foreign Application Priority Data

Jun. 3, 2002 (JP) .............................. 2002-161626

(51) Int. Cl.
*A61B 18/18* (2006.01)
(52) U.S. Cl. ........................................ 606/33; 607/156
(58) Field of Classification Search ............ 606/27–52; 607/156
See application file for complete search history.

(56) References Cited

U.S. PATENT DOCUMENTS

2001/0044575 A1 11/2001 Hareyama et al.

FOREIGN PATENT DOCUMENTS

EP 202362 11/1986
JP 339772 6/1991

OTHER PUBLICATIONS

Patent Abstracts of Japan "Manufacture of Collar" English Translation 01-224133 Jul. 9, 1989 Hasegawa Shiro.

*Primary Examiner*—Michael Peffley
*Assistant Examiner*—Pete Vrettakos
(74) *Attorney, Agent, or Firm*—Miller, White, Zelano, Branigan, P.C.

(57) ABSTRACT

Disclosed is an electrode device for microwave surgery which is provided with a marker securely fixed to the central electrode, which marker can provide a magnetic susceptibility artifact of a uniform size and shape free of fluctuation among electrode devices. The electrode device comprise a central conductor body, a tubular insulator body which covers the central conductor body except its distal end, a tubular external electrode which covers the tubular insulator body except its distal end part, and a central electrode which covers the distal end part of the central conductor body. The central conductor body, the insulator body, the external electrode and the central electrode are made of a nonmagnetic material, and a cylindrical member made of a magnetic material is fit around the distal end part of the central conductor body. At least one projection is defined on the lateral face of the central conductor body at the distal side of the cylindrical member, and the cylindrical member engages with the projection in the distal direction.

11 Claims, 7 Drawing Sheets

ELECTRODE DEVICE FOR MICROWAVE SURGERY

TECHNICAL FIELD

The present invention relates to an electrode device suited for use in microwave surgery performed under MRI (magnetic resonance imaging) monitoring. More specifically, the present invention relates to an electrode device to be used in a microwave surgery instrument, which, using microwave, performs coagulation of a biotissue, arrests hemorrhages and carries out partial excision, which electrode device can cause to generate an artifact that is uniform in size and shape free of fluctuation among electrode devices, on a MRI monitor screen displaying the site that is undergoing an operation.

BACKGROUND ART

Microwave surgery is a technique to selectively coagulate affected part of the body, arrest hemorrhages and perform partial excision utilizing dielectric heat generated in a tissue of the body by a localized microwave electromagnetic field created between electrodes which are inserted in the affected part of the body and between which a microwave of a predetermined frequency is emitted. As to microwave surgery of a deep site of the body, percutaneous microwave coagulation therapy (PMCT) and laparoscopic microwave coagulation therapy (LMCT) are widely applied. A recent development of an open-type MRI apparatus has enabled microwave surgery to be conducted under real-time observation of the affected site utilizing such a MRI apparatus. Microwave electrode devices for this purpose are made of a material substantially inert to the magnetic field created by the MRI apparatus, i.e., a nonmagnetic material so that they do not hinder monitoring of the affected site. Thus, it has been difficult to detect inserted microwave electrode devices on a MRI monitor screen.

The difficulty in detecting a microwave electrode device on the MRI monitor screen, however, causes inconvenience for the surgeon that he or she can not identify, on the MRI monitor screen, the position of the microwave electrode inserted in the body relative to the affected site. To address this problem, a method has been conceived in which a marker of magnetic material is attached near the distal end of the electrode device to induce a magnetic susceptibility artifact (hereinafter referred to simply as an "artifact"), which is an area observed black around the marker on the MRI monitor screen, thereby making it easier to roughly identify, on the MRI monitor screen, the position of the coagulating or cauterizing electrode device in the body. For this, it is proposed to place solder, metal plating such as titanium coating, and a mounted ring member as markers (Japanese Patent Application Publication No. H11-267133).

However, with solder or metal plating, it is difficult to control the amount of the marker to be placed on microwave electrode devices, and, therefore, fluctuation in marker amount among microwave electrode devices is hard to eliminate. Fluctuation among electrode devices in the amount of the placed solder or titanium coat causes fluctuation in the size of the artifact. As a general rule, electrode devices for microwave surgery are disposed of after a single use of them for safety requirements such as prevention of transmission, surgeons are forced to use new electrodes in each operation. A MRI monitoring screen displays only a specific cross section of the body. Consequently, the size of the artifact is greatest when a marker is positioned on this specific cross section, and the artifact reduces its size or eliminates when the marker deviates from the specific cross section as a function of the distance from it. If there is fluctuation in the size of generated artifact among electrode devices, a surgeon, who manipulates an electrode device relying on the position and the size of the artifact, must identify in every operation the maximal diameter of the artifact induced by the electrode device used while using the very electrode device and then reflect this to his manipulation. This causes a great deal of inconvenience and impedes achieving the uniformity of manipulation.

In addition, in order to keep coagulated tissues from adhering to the microwave electrode device being used, a fluorocarbon resin is coated on the electrode device. As the baking temperature for this (about 390° C.) is what solder (melting at about 200° C.) cannot stand, use of solder as a marker would cause a trouble in application of fluorocarbon resin coating. Furthermore, when water is lost from tissues being cauterized in an operation, the electrodes could reach high temperatures, and this, due to the melting of the solder, could lead to risks of leaking and falling of the solder on the lesion.

In the case where a ring member is to be mounted as a marker, there is a problem of how to securely fix the member to prevent it from loosening or falling. That is, in microwave surgery now, needle-like devices are used because of year-to-year request for thinner, needle-like electrode devices. Thus, where an electrode with small diameter is inserted in a ring-shaped marker member, it would become necessary to securely fix the marker member onto the electrode. A screw or other components cannot be applied, however, due to the small diameter of the electrode. As for welding, arc welding cannot be applied, for it would not only cause an uncontrollable extra artifact due to added welding materials but also lead to reduction in the strength of the electrode due to residual stress. Although application of spot welding could evade the problems of an extra artifact and reduction in the strength, it is difficult to securely fix the ring-shaped member by spot welding alone. Otherwise, spot welding applied in excess also could lead to reduction in the strength of the electrode due to remaining stress. Moreover, for easiness of an operation, a marker is to be mounted preferably onto the central conductor body at the tip of the electrode device. However, because of the narrow diameter of the central conductor body, it is much more difficult to securely fix a marker ring onto the central conductor body. And further, when the tip of the electrode device is burnt and bonded to a cauterized tissue, it is necessary to manipulate the electrode device to detach its tip from the biotissue, in the process of which stress is concentrated on the tip of the electrode device. In case the marker ring is not securely fixed onto the central conductor body, it could lead to an event that the marker detaches due to the stress and falls together with the central electrode covering the marker.

As electrode device, as a general rule, is to be disposed of after each operation, means for securely fixing the marker must be simple and applicable at low costs so as not to be a factor that could cause a price rise of the device.

DISCLOSURE OF INVENTION

Against the background mentioned above, the objective of the present invention is to provide, by a simple and therefore low-cost method, an electrode device for microwave surgery, which can be used in microwave surgery performed under monitoring on a MRI apparatus and which is provided with a marker which can give an artifact that is uniform in size and shape free of fluctuation among electrode devices and is securely fixed onto the central conductor body.

Through suitable defining of the shape of a marker member together with finding of a well-suited way of binding a central conductor body and the marker member, the present inventors succeeded in creating an electrode device for microwave surgery which achieves the above-mentioned objective.

Thus, the present invention provides an electrode device for microwave surgery comprising a central conductor body, a tubular insulator body which covers the central conductor body except distal end part of the central conductor body, a tubular external electrode which covers the tubular insulator body except distal end part of the tubular insulator body, and a central electrode which covers the distal end part of the central conductor body, wherein any of the central conductor body, the tubular insulator body, the tubular external electrode and the central electrode is made of a nonmagnetic material, and a cylindrical member made of a magnetic material is fit around the distal end part of the central conductor body, at least one projection is defined on the lateral face of the central conductor body on the distal side of the cylindrical member, and the cylindrical member engages with the projection in the distal direction.

According to the present invention, a cylindrical member, which is a marker of a magnetic material readily and definitely formed to have a uniform mass and a uniform shape, can be incorporated, in a securely fixed form, in a microwave electrode device made of nonmagnetic materials by enabling the cylindrical member to engage with the projection of the central conductor body. Thus, if the cylindrical member receives a strong tensile force in the distal direction, there will be no risk of falling off of the marker or the central electrode covering it, for any displacement of the cylindrical member in the distal direction is prohibited by the engagement. In addition, the present invention gives an artifact that is uniform in size and shape and free of fluctuation among electrode devices in an operation under monitoring on a MRI apparatus. Furthermore, as the marker can be securely fixed in a simple manner, the present invention can be practiced at a low cost.

The present invention further provides an electrode device for microwave surgery described above, wherein the engagement of the cylindrical member with the projection is made by meshing, with the projection, of at least one notch defined in the cylindrical member at the distal side thereof.

The present invention further provides an electrode device for microwave surgery, wherein a pair of projections are defined on the opposite side of the lateral face of the central conductor body, and the engagement of the cylindrical member with the pair of projections is made by meshing of the pair of projections with a pair of notches defined in the cylindrical member on the distal side thereof at positions facing the projections.

The present invention further provides any one of the above-described electrode devices for microwave surgery, wherein the cylindrical member defines an opening in the intermediate area of the lateral face thereof.

The present invention further provides any one of the electrode devices for microwave surgery described above, wherein the cylindrical member includes an overhanging portion formed by extending part of the circumference on the distal or proximal side of the cylindrical member in the longitudinal direction.

The present invention further provides any one of the above-described electrode devices for microwave surgery, wherein the cylindrical member further defines a slit extending in the longitudinal direction through the both ends thereof.

The present invention further provides an electrode device for microwave surgery, wherein a pair of projections are defined on the opposite sides of the lateral face of the central conductor body, wherein the cylindrical member includes an overhanging portion formed by extending part of the circumference on the distal side of the cylindrical member in the longitudinal direction, the overhanging portion unrotatably engaging at each of the both lateral edges with each of the pair of projections, wherein the front edge of the cylindrical member engages at the foot of the overhanging portion with the projections in a manner where displacement of the front edge in the distal direction is prohibited.

Still more, the present invention provides any one of the above-described electrode devices for microwave surgery, wherein the front edge of the cylindrical member includes notches facing the pair of projections at the foot of the overhang portion, and the projections engage with the notches.

The present invention still further provides any one of the above-described electrode devices for microwave surgery, wherein spot welding is made between the cylindrical member and the central conductor body.

The present invention further provides any one of the above-described electrode devices for microwave surgery, wherein the cylindrical member is made of stainless steel.

The present invention further provides any one of the above-described electrode devices for microwave surgery, wherein the mass of the cylindrical member is 1–10 mg.

BEST MODE FOR CARRYING OUT THE INVENTION

In the present invention, the term a "magnetic material" means such a material that has a level of magnetic susceptibility enough to induce an artifact in images being monitored by MRI. Examples of it include stainless steel (SUS), nickel alloys (cupronickel), copper-nickel-zinc alloys (brass+nickel (10–20%), cobalt-chromium alloys, etc.

In the present invention, the term a "nonmagnetic material" means a material that has such a limited magnetic susceptibility that can not induce an artifact in MRI images. Examples of it includes brass (cupper+tin), phosphor bronze (cupper+tin+phosphor), copper, zinc, gold, silver alloys, etc.

Under a constant imaging condition, the size of an artifact correlates to the material and mass of the cylindrical member used as a marker. For example, in the case of stainless steel (SUS 304), 1–10 mg, or more preferably 3–10 mg of it can induce an artifact of a moderate size in MRI monitoring images. However, the material and the mass of the marker may be determined as desired in accordance with the size of the artifact requested. In any case, the present invention enables to securely fix a marker of a precise amount of mass to provide electrode devices that gives uniformly sized artifacts that are free of device-to-device fluctuation.

In the present invention, an additional marker member may also be attached at another position, e.g., in the intermediate part of the central conductor body. In this case, the plural artifacts induced by the plural marker members make it easier to see the relative positions and orientation of the affected site and the electrode device.

EXAMPLES

The present invention will be described in further detail below with reference to examples. It is not intended, however, that the present invention be limited by the examples. In the figures, each reference number indicates: 1=monopolar electrode device for microwave surgery, 2=coaxial cable connector, 3=external electrode, 4=insulator body, 5=central electrode, 6=central conductor body, 7=marker member, 8=projection, 9=overhanging portion, 12=notch, 17=marker member, 19=overhanging portion, 22=notch, 27=marker member, 32=notch, 33=opening, 37=marker member, 42=notch, 44=slit, 47=marker member.

Example 1

Figure 1:
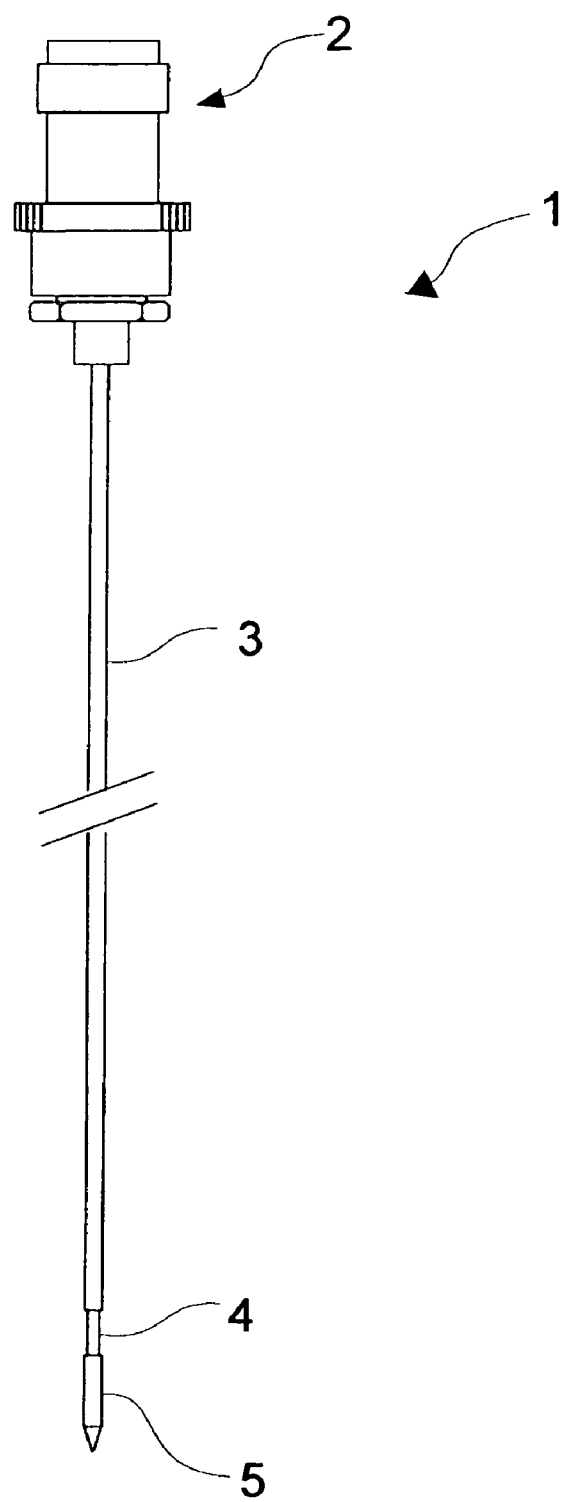
FIG. 1 is a general view of an electrode device for microwave surgery.

FIG. 1 illustrates a general view of a needle-like monopolar electrode device 1 for microwave surgery of this example. In the electrode device 1, numeral 2 indicates a coaxial cable connector, numeral 3 a cylindrical external electrode, numeral 4 a tubular insulator body extending through the external electrode 3, and numeral 5 a central electrode. A coating of fluorocarbon resin is applied to cover the entirety of external electrode 3, insulator body 4 and central electrode 5. The distance from the root of the external electrode to the tip of the central electrode is 252 mm, the external diameter of the external electrode and the central electrode 1.6 mm, the length of the central electrode 10 mm, and the length of the exposed part of the insulator body 6 mm.

Figure 2:
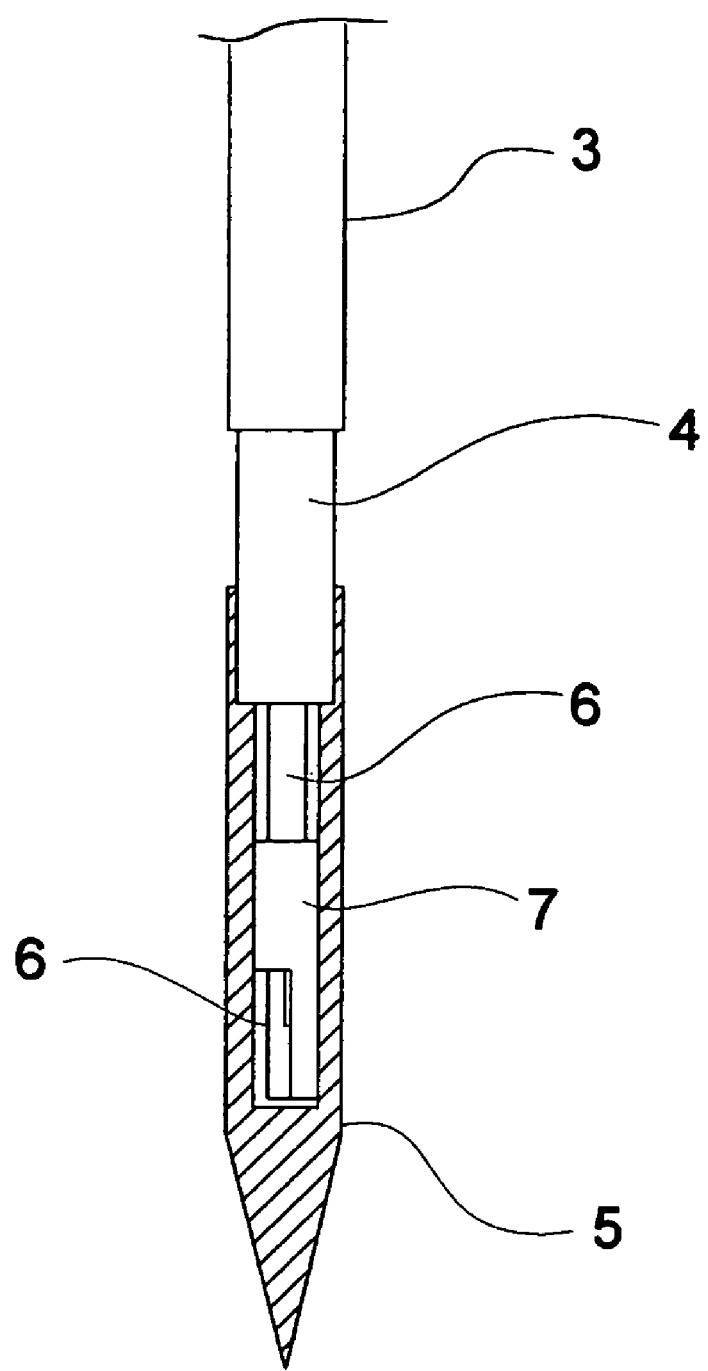
FIG. 2 is an enlarged view of a distal region of the electrode device of Example 1 including a partial cross sectional view.

FIG. 2 illustrates an enlarged view of a distal area of the electrode device 1 shown in FIG. 1 including a partial cross sectional view. In the figure, the external electrode 3 is made of brass plated with gold, the tubular insulator body 4 of a fluorocarbon resin PTFE (Teflon (trademark)), and the central electrode 5 of phosphor bronze plated with gold. The central electrode 5, which defines a conical sharp tip at its distal end for piercing tissues, has a generally cylindrical cavity, into proximal part of which the distal end part of the insulator body 4 is fit. In the cavity of the central electrode 5 is inserted the distal end part of the central conductor body 6 which extends through the insulator body 4 and protrudes from the distal end thereof. The central conductor body 6 is made of phosphor bronze plated with silver. On the central conductor body 6 is fixed, in a manner mentioned later, a cylindrical marker member 7 of stainless steel (SUS 304) for inducing an artifact in MRI monitoring images. The central electrode 5 which covers the marker member 7 is securely fixed on it by swaging from outside at frontal and rear positions of the marker member 7. Thus, the central conductor body 6, the marker member 7 and the central electrode 5 are combined, and the central electrode 5 is electrically integrated with the central conductor body 6 via the marker member 7.

Figure 3:
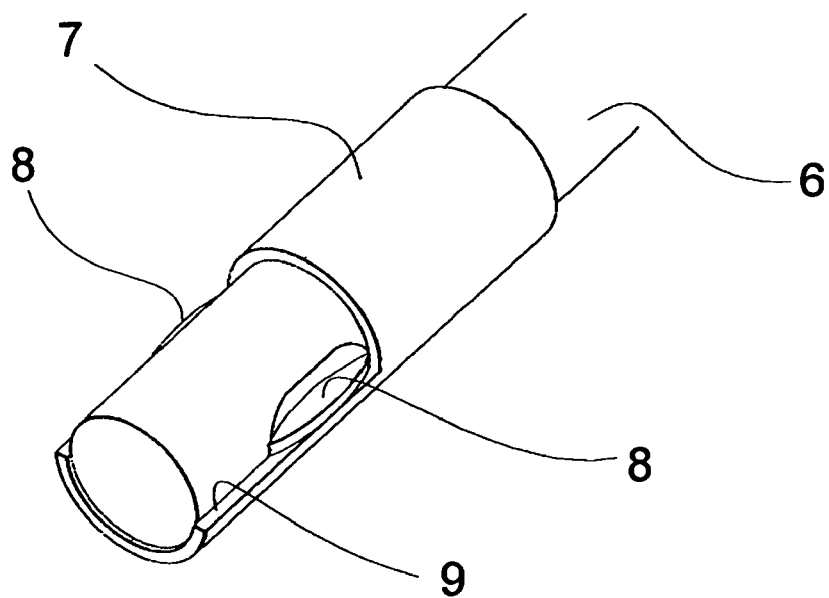
FIG. 3 is a perspective view of the marker member of Example 1 coupled to the central conductor body.
Figure 4:
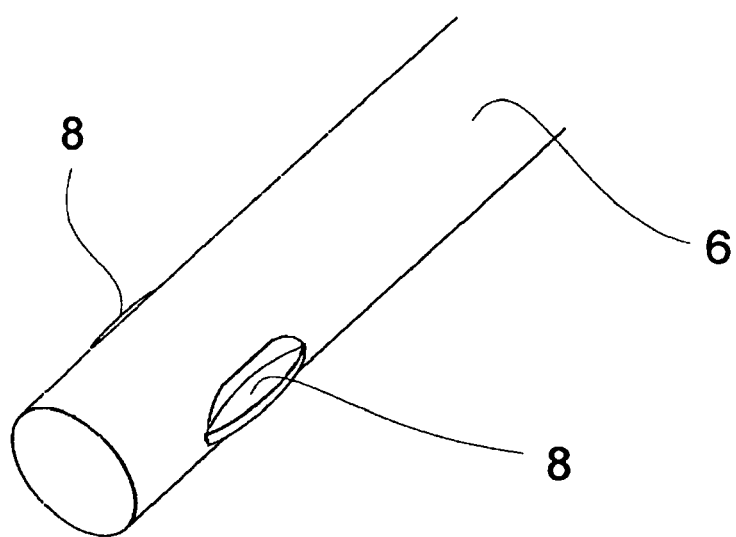
FIG. 4 is a perspective view of the central conductor body of Example 1.
Figure 5:
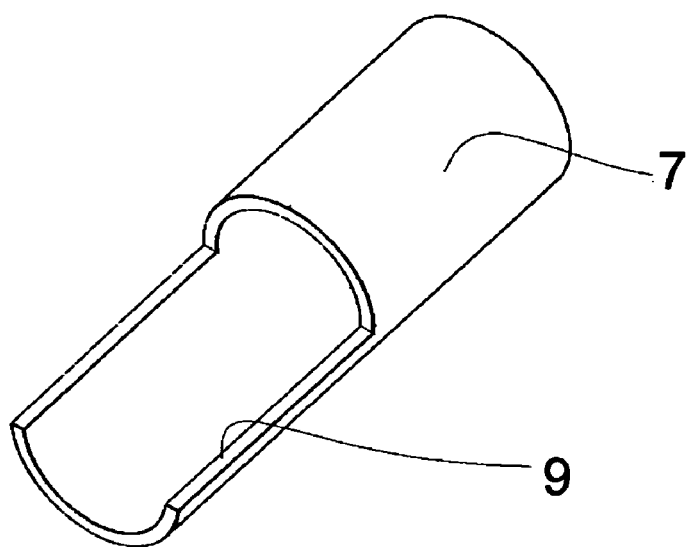
FIG. 5 is a perspective view of the marker member of Example 1.

FIGS. 3–5 illustrates the manner of secure fixation of the central conductor body 6 and the marker member 7 within the central electrode 5. As seen in the figures, there are provided a pair of oppositely directed projections 8 on the lateral face of the central conductor body 6 near the distal end thereof. The height of the projections 8 is designed so that the tops of the projections 8 are roughly flush with the outer surface of the marker member 7. Although the projections 8 may be formed by any way as desired in this example, they are formed by pinching the central electrode between dies to allow plastic deformation to occur.

The marker member 7 (1 mm in outside diameter, 3 mm in length, 6 mg in mass) includes a cylindrical portion on its proximal side through which the central conductor body 6 is to be passed and a overhanging portion 9 which is formed by extending part of the circumference of the cylindrical portion forward in the longitudinal direction. The shape and dimensions of the marker member 7 including the overhanging portion 9, and those of the central conductor body 6 including the projections 8, are designed so that, when the marker member 7 is slid forward on the central conductor body 6 up to the position illustrated in FIG. 3, the upper surfaces of the both lateral edges of the overhanging portion 9 of the marker member 7 come into contact with the lower surfaces of the pair of projections 8 on the central conductor body 6, and that the rear edges of the pair of projections 8 come into contact with the front edges of the cylindrical portion of the marker member 7. Thus, in the position illustrated in FIG. 3, the marker member 7 is blocked, by its engagement with the pair of projections 8, from shifting forward along the central conductor body 6 and from rotating around the axis relative to the central conductor body 6. Further, spot welding is performed between the marker member 7 and the central conductor body 6, thereby blocking backward sliding of the marker member 7 relative to the central conductor body 6 and electrically integrating them. The spot welding may be made by applying spot welding electrodes onto the exposed surface of the central conductor body 6 over the overhanging portion 9 of the marker member 7 and any surface of the marker member 7, e.g., the lower surface of the overhanging portion 9. This manner of secure fixation of the marker member 7 onto the central conductor body 6 provides such a firm binding between the central conductor body 6 and the marker member 7 that is sufficient to bear external forces that can be applied between the central conductor body 6 and the marker member 7 in a variety of stages during microwave surgery, inter alia, twisting and tensile external forces that otherwise could cause troubles.

Testing under MRI monitoring:

Ten grams of agar were added to 500 ml of physiological saline, completely dissolved by heating and stirring, then poured into a mold and allowed to cool to give an agar block for use in place of an affected site.

The above-obtained agar block was placed in an open-type MRI apparatus (SIGMA SP/i, 0.5 tesla, manufactured by General Electric Company). Under MRI monitoring using the gradient echo method, the electrode device for microwave surgery of the present example was inserted along the agar block's cross section being monitored by MRI. On the monitor screen, an artifact with a clear boundary seen as a nearly circular black hollow of about 10 mm in diameter was clearly observed to move, in a homogenous gray cross section of the agar block that emerged in a black background, as the electrode device was inserted.

Example 2

Figure 6:
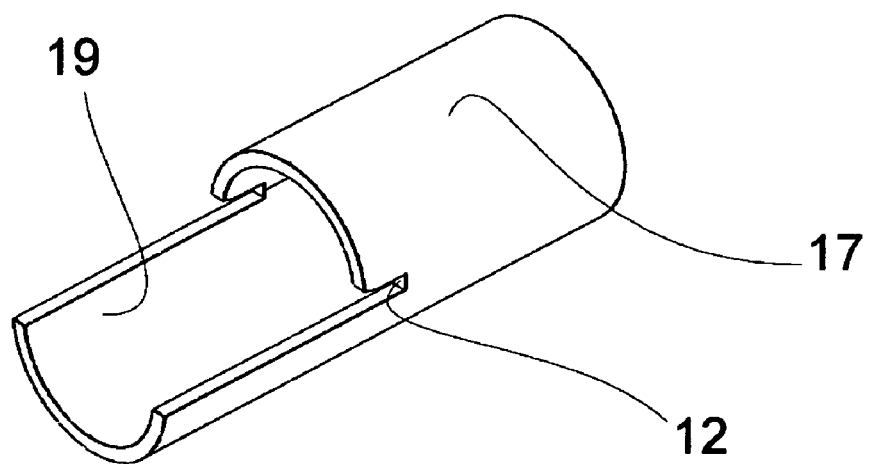
FIG. 6 is a perspective view of the marker member of Example 2.
Figure 7:
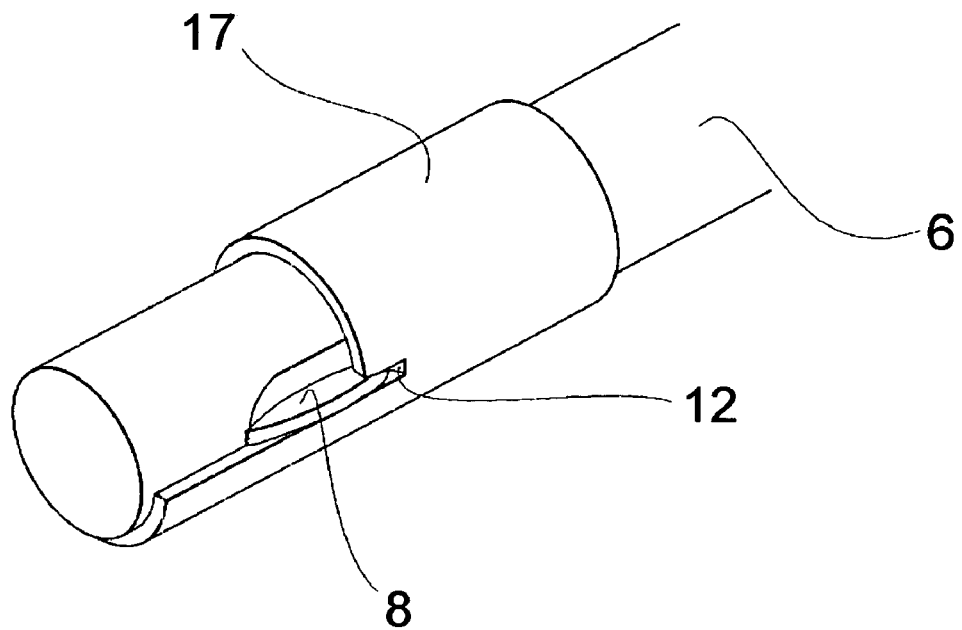
FIG. 7 is a perspective view of the marker member of Example 2 coupled to the central conductor body.

FIG. 6 illustrates the shape of the marker member 17 used in this example, and FIG. 7 the marker member 17 as secured onto the central conductor body 6. Except the shape of the marker member 17, the components of this example are identical to those of Example 1, and spot welding also is performed as in Example 1. The marker member 17 includes a cylindrical portion on its proximal side, through which the central conductor body 6 is to be passed, and an overhanging portion 19 which is formed by extending part of the circumference of the cylindrical portion in the longitudinal direction, and defines a pair of notches 12 in the front edge of the cylindrical portion at the foot of the overhanging portion 9. The shape and the dimensions of the notches 12, as seen in FIG. 7, are designed so as to allow engagement with the projections 8 on the central conductor body 6. In this example, the notches 12 engage with the projections 8 on the central conductor body 6 and each of the projections 8 contacts, on its upper and lower surfaces, with the upper and lower surfaces of one of the notches 12 (and with an upper surface of either of the lateral edges of the overhanging portion 19), thereby achieving securer fixation against twisting.

Example 3

Figure 8:
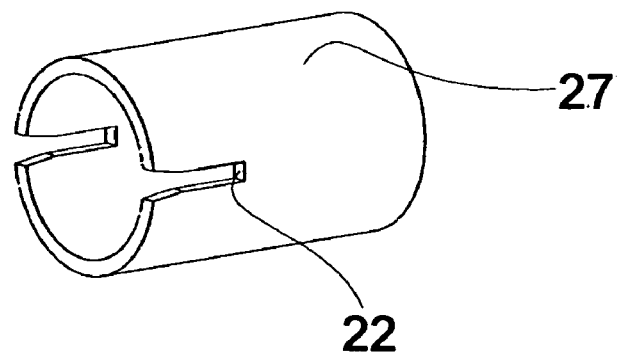
FIG. 8 is a perspective view of the marker member of Example 3.

FIG. 8 illustrates the shape of the marker member 27 used in this example. Except the shape of the marker member, this example is identical to Example 1. The marker member 27 is generally cylindrical and defines notches 22 for receiving and engaging with the corresponding part of the pair of projections 8 provided on the central conductor body 6. Spot welding is performed by applying electrodes to an exposed surface of the central conductor body 6 and any surface of the marker member. This example achieves as firm a fixation as Example 2, for the pair of projections 8 on the central conductor body 6 are fit in the notches 22 of the marker member 27.

Example 4

Figure 9:
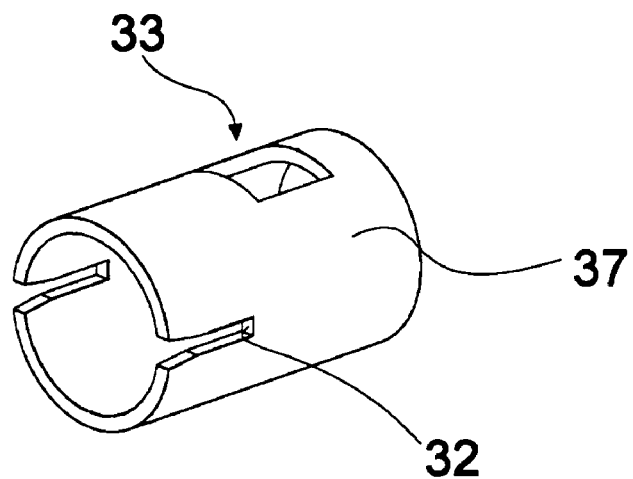
FIG. 9 is a perspective view of the marker member of Example 4.

FIG. 9 illustrates the shape of the marker member 37 used in this example. Except the shape of the marker member, this example is identical to Example 1. The marker member 37 in this example, as in Example 3, is generally cylindrical and defines notches 32 for receiving and engaging with the corresponding part of the pair of projections 8 provided on the central conductor body 6, and further defines in its lateral face an opening 33 which is not present in the marker member 27 in Example 3. When the marker member 37 is placed on the central conductor body 6 at a predetermined position, the opening provides a convenient surface for applying one of the welding electrodes for carrying out spot welding, by exposing part of the central conductor body 6 under the marker member 37. The other of the electrodes may be applied to, e.g., the lower face of the marker member 37.

Example 5

Figure 10:
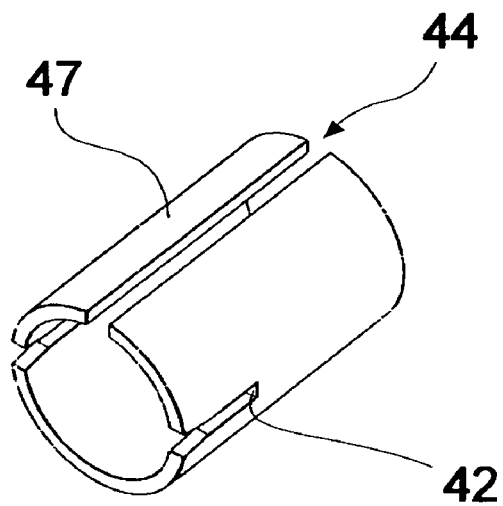
FIG. 10 is a perspective view of the marker member of Example 5.
Figure 11:
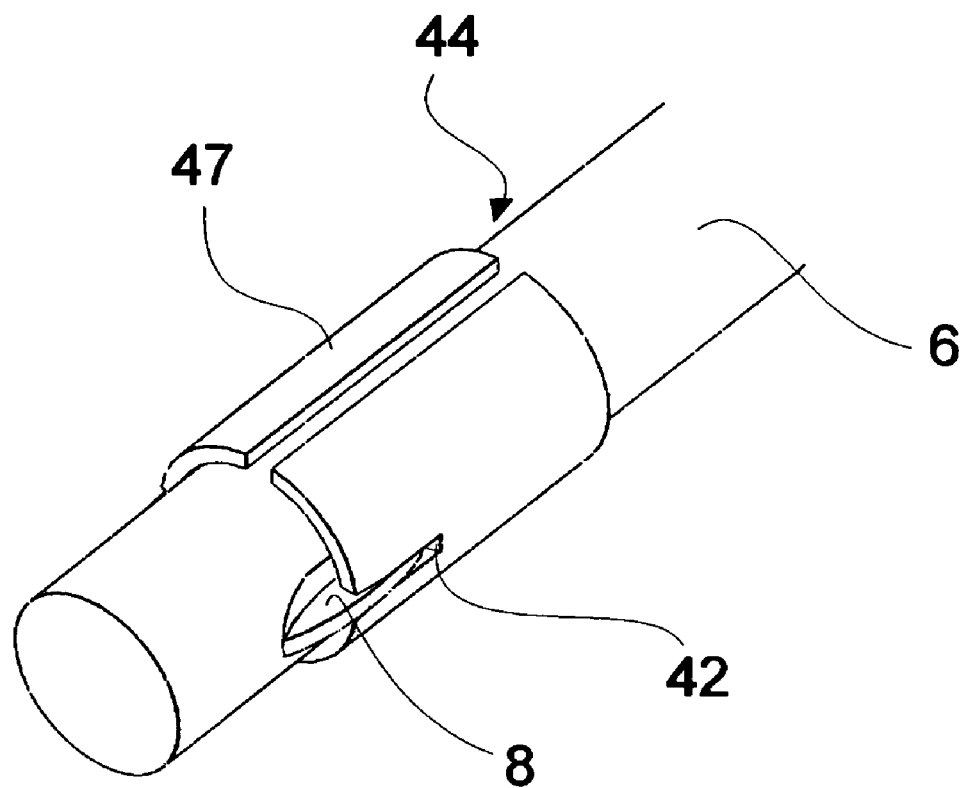
FIG. 11 is a perspective view of the marker member of Example 5 coupled to the central conductor body.

FIG. 10 illustrates the shape of the marker member 47 used in this example, and FIG. 11 the marker member 47 as attached onto the central conductor body 6. Except for the shape of the marker member 47, the components of this example are identical to those of Example 1. The marker member 47, as the marker member 27 in Example 3, is generally cylindrical and defines notches 42 for receiving and engaging with the corresponding part of the pair of projections 8 provided on the central conductor body 6, and further defines in its lateral face a slit 44 extending in the longitudinal direction through the both ends, which is not present in the marker member 27 in Example 3. The slit 44 provides, in the gap defined by it, an exposed surface of the central conductor body 6, which may be utilized as desired to apply a welding electrode to the central conductor body 6 in carrying out spot welding of the marker member 47 and the central conductor body 6. The width of the slit 44 of the marker member 47 will not be expanded by external forces conceivable to the electrode device, for the marker member 47 fixed onto the central conductor body 6 is squeezed by the internal surface of the central electrode 5 by swaging the central electrode 5, which closely covers the marker member 47, from outside at frontal and rear positions of the marker member 47. Therefore, the presence of the slit 44 does not affect the secure fixation of the marker member 47 and the central conductor body 6, and the marker member in this example is thus fixed as firmly as in other examples.

INDUSTRIAL APPLICABILITY

According to the present invention, an electrode device for microwave surgery is provided which can be used in microwave surgery performed under monitoring on a MRI apparatus and which comprises a securely fixed marker which provides an artifact of a uniform size and shape free of fluctuation among electrode devices.

The invention claimed is:

1. An electrode device for microwave surgery comprising a central conductor body, a tubular insulator body which covers the central conductor body except distal end part of the central conductor body, a tubular external electrode which covers the tubular insulator body except distal end part of the tubular insulator body, and a central electrode which covers the distal end part of the central conductor body, wherein
    any of the central conductor body, the tubular insulator body, the tubular external electrode and the central electrode is made of a nonmagnetic material, and a cylindrical member made of a magnetic material is fit around the distal end part of the central conductor body,
    at least one projection is defined on the lateral face of the central conductor body on the distal side of the cylindrical member, and
    the cylindrical member engages with the projection in the distal direction.

2. The electrode device for microwave surgery of claim 1, wherein the engagement of the cylindrical member with the projection is made by meshing, with the projection, of at least one notch defined in the cylindrical member at the distal side thereof.

3. The electrode device for microwave surgery of claim 1, wherein a pair of projections are defined on the opposite side of the lateral face of the central conductor body, and the engagement of the cylindrical member with the pair of projections is made by meshing of the pair of projections with a pair of notches defined in the cylindrical member on the distal side thereof at positions facing the projections.

4. The electrode device for microwave surgery of claim 1, wherein an opening is defined in the intermediate area of the lateral face of the cylindrical member.

5. The electrode device for microwave surgery of claim 1, wherein the cylindrical member further defines a slit extending in the longitudinal direction through the both ends thereof.

6. The electrode device for microwave surgery of claim 1, wherein the cylindrical member includes an overhanging portion formed by extending part of the circumference on the distal or proximal side of the cylindrical member in the longitudinal direction.

7. The electrode device for microwave surgery of claim 1, wherein a pair of projections are defined on the opposite sides of the lateral face of the central conductor body, wherein the cylindrical member includes an overhanging portion formed by extending part of the circumference on the distal side of the cylindrical member in the longitudinal direction, the overhanging portion unrotatably engaging at each of the both lateral edges with each of the pair of projections, wherein the front edge of the cylindrical member engages at the foot of the overhanging portion with the projections in a manner where displacement of the front edge in the distal direction is prohibited.

8. The electrode device for microwave surgery of claim 7, wherein the front edge of the cylindrical member includes notches facing the pair of projections at the foot of the overhang portion, and the projections engage with the notches.

9. The electrode device for microwave surgery of claim 1, wherein spot welding is made between the cylindrical member and the central conductor body.

10. The electrode device for microwave surgery of claim 1, wherein the cylindrical member is made of stainless steel.

11. The electrode device for microwave surgery of claim 1, wherein the mass of the cylindrical member is 1–10 mg.

* * * * *